(12) United States Patent
Deshpande et al.

(10) Patent No.: US 11,243,167 B2
(45) Date of Patent: Feb. 8, 2022

(54) METHODS AND SYSTEMS FOR ASSESSING A HEALTH STATE OF A LACTATING MAMMAL

(71) Applicant: SomaDetect Inc., Fredericton (CA)

(72) Inventors: Bethany Deshpande, Fredericton (CA); Nicholas Clermont, Fredericton (CA); Satish Deshpande, Guelph (CA); Bharath Sudarsan, Fredericton (CA); Bryan Wattie, Sackville (CA)

(73) Assignee: SomaDetect Inc., Fredericton (CA)

( * ) Notice: Subject to any disclaimer, the term of this patent is extended or adjusted under 35 U.S.C. 154(b) by 53 days.

(21) Appl. No.: 16/639,885

(22) PCT Filed: Aug. 17, 2018

(86) PCT No.: PCT/CA2018/051003
§ 371 (c)(1),
(2) Date: Feb. 18, 2020

(87) PCT Pub. No.: WO2019/033221
PCT Pub. Date: Feb. 21, 2019

(65) Prior Publication Data
US 2020/0363333 A1 Nov. 19, 2020

Related U.S. Application Data

(60) Provisional application No. 62/547,393, filed on Aug. 18, 2017.

(51) Int. Cl.
*G01N 21/51* (2006.01)
*A61D 99/00* (2006.01)
*G01N 21/47* (2006.01)

(52) U.S. Cl.
CPC ............. *G01N 21/51* (2013.01); *A61D 99/00* (2013.01); *G01N 2021/4707* (2013.01); *G01N 2201/1296* (2013.01)

(58) Field of Classification Search
CPC ........ G06T 7/0012; G06T 2207/30024; G06K 9/0014; G01N 15/0205; G01N 21/51;
(Continued)

(56) References Cited

U.S. PATENT DOCUMENTS 6,315,955 B1 11/2001 Klein
7,736,588 B2 6/2010 Langeveld et al.
(Continued)

FOREIGN PATENT DOCUMENTS

WO        0049388      8/2000
WO    2004/017066 A1  2/2004
(Continued)

OTHER PUBLICATIONS

Jain et al. Light scattering and transmission measurement using digital imaging for online analysis of constituents in milk: Jun. 22, 2015: https://www.spiedigitallibrary.org/conference-proceedings-of-spie/9525/95254A/Light-scattering-and-transmission-measurement-using-digital-imaging-for-online/10.1117/12.2184903.short?SSO=1.

(Continued)

*Primary Examiner* — Hoa Q Pham
(74) *Attorney, Agent, or Firm* — Norton Rose Fulbright Canada LLP

(57) ABSTRACT

Methods and systems for detecting the presence of irregularities in milk, and for assessing a health state of a lactating mammal, are provided. A sample of milk is illuminated with a light beam. Scattering data resulting from an interaction between the light beam and the sample of milk is collected. The scattering data is processed to detect the presence or absence of light scattered at a predetermined angle relative to a normal orientation, for instance to determine at least one characteristic of the sample of milk. Based on the presence or absence of light, the presence of irregularities in the
(Continued)

sample of milk can be determined, for instance to assess the health state of the lactating mammal based on the at least one characteristic of the sample of milk.

20 Claims, 10 Drawing Sheets

(58) Field of Classification Search
CPC ............... G01N 21/00; G01N 21/31; G01N 2021/4707; G01N 33/00; G01N 33/04; G01N 33/487; G01N 33/06; A01J 5/0133; A01J 5/01; A01J 5/08; A61D 99/00
USPC ......... 356/335–343, 72, 319; 324/71.4, 637; 119/14.01–14.55; 426/33–41, 231
See application file for complete search history.

(56) References Cited

U.S. PATENT DOCUMENTS

| | | | |
|---|---|---|---|
| 7,790,467 B1* | 9/2010 | Massick | G01N 33/497 436/130 |
| 8,103,080 B2* | 1/2012 | George | G06K 9/00127 382/133 |
| 8,213,007 B2 | 7/2012 | Wang et al. | |
| 9,389,175 B2 | 7/2016 | Deshpande | |
| 9,415,392 B2 | 8/2016 | Ismagilov et al. | |
| 9,459,252 B2 | 10/2016 | Gabriel | |
| 2003/0098409 A1* | 5/2003 | Bond | G01N 21/59 250/223 R |
| 2004/0179194 A1* | 9/2004 | Schmilovitch | G01N 21/3577 356/244 |
| 2009/0255473 A1 | 10/2009 | Katz | |
| 2014/0139834 A1* | 5/2014 | Deshpande | G01N 21/51 356/338 |
| 2019/0120760 A1* | 4/2019 | Lai | G01N 33/14 |

FOREIGN PATENT DOCUMENTS

| | | |
|---|---|---|
| WO | 2017041129 | 3/2017 |
| WO | 2017065708 | 4/2017 |
| WO | 2017085162 | 5/2017 |
| WO | 2017089727 | 6/2017 |
| WO | 2017171650 | 10/2017 |
| WO | 2018111094 | 6/2018 |

OTHER PUBLICATIONS

Kim et al. Melamine Sensing in Milk Products by Using Surface Enhanced Raman Scattering: Anal. Chem. 2012, 84, 21, 9303-9309: Publication Date:Oct. 8, 2012: https://pubs.acs.org/doi/abs/10.1021/ac302025q#.
Extended European Search Report dated May 10, 2021 issued in EP 18846855.7.
Aernouts, B. et al., "Visible and near-infrared bulk optical properties of raw milk", Journal of Dairy Science, vol. 98, No. 10, Jul. 22, 2015, pp. 6727-6738, XP055400305.
Dahm, Donald J., "Explaining Some Light Scattering Properties of Milk Using Representative Layer Theory", Journal of Near Infrared Spectroscopy, vol. 21, No. 5, Oct. 15, 2013, pp. 323-339, XP055799590.

* cited by examiner

METHODS AND SYSTEMS FOR ASSESSING A HEALTH STATE OF A LACTATING MAMMAL

CROSS-REFERENCE TO RELATED APPLICATIONS

This application is a national stage entry of PCT/CA2018/051003 filed Aug. 17, 2018, which claims the benefit of and priority to U.S. Provisional Application 62/547,393, entitled "METHODS AND SYSTEMS FOR ASSESSING A HEALTH STATE OF A LACTATING MAMMAL", filed Aug. 18, 2017, the contents of which are incorporated herein by reference.

TECHNICAL FIELD

The present disclosure relates generally to milk production, and more particularly to light-scattering-based analysis of milk.

BACKGROUND

The quality of milk produced by a lactating mammal is dependent on a number of factors, such as the health of the animal, nutrition, immune status, physical factors that contribute to well-being such as shelter, access to quality food and water, and emotional security, among others. In a commercial setting, the ability to gauge and optimize these factors is important, since improved animal health leads to higher profit margins due to improved milk quality and reduced operational costs.

Milk producers already face significant challenges with falling milk prices, increased labor costs, and demanding regulatory regimes, especially concerning the presence of antibiotics and the like in milk. Traditional means for tracking the health of a lactating mammal are invasive, time-consuming, and not typically automated, requiring increased personnel with a certain degree of expertise. In addition, valuable information regarding the health of the lactating mammal may be contained in the milk it produces, but typically requires chemical testing to obtain. This chemical testing may not be easily performed on-site, which can lead to long delays before the information can be acted upon. Moreover, certain stringent regulatory regimes require the destruction of entire batches of milk for even the nominal presence of antibiotics or blood components.

As such, there is room for improved techniques for testing milk and for assessing the health state of a lactating mammal.

SUMMARY

In accordance with a broad aspect, there is provided a method for assessing a health state of a lactating mammal. A sample of milk obtained from the lactating mammal is illuminated with a light beam. Scattering data resulting from an interaction between the light beam and the sample of milk is collected. The scattering data is processed to determine at least one characteristic of the sample of milk. The health state of the lactating mammal is assessed based on the at least one characteristic of the sample of milk.

In some embodiments, the scattering data is indicative of light from the light beam being scattered along at least a first scattering angle greater than 0.5°.

In some embodiments, the light beam comprises light of at least a first wavelength and a second wavelength.

In some embodiments, the scattering data is indicative of light from the light beam being scattered along at least a first scattering angle associated with the first wavelength and of light from the light beam being scattered along a second scattering angle associated with the second wavelength, wherein the scattering data comprises a plurality of data sets each associated with a respective scattering angle.

In some embodiments, processing the scattering data comprises comparing the scattering data with angular profiles of reference milk samples having known characteristics.

In some embodiments, processing the scattering data comprises comparing the standard deviation of pixel intensity for a set of scattering profiles against the standard deviation of pixel intensity for a previous set of scattering profiles.

In some embodiments, processing the scattering data comprises processing the scattering data using a neural network.

In some embodiments, the method further comprises training the neural network using reference milk samples having known characteristics.

In some embodiments, the at least one characteristic of the sample of milk comprises at least one of a fat content, a fat-to-protein ratio, an antibiotic content, a blood content, and a somatic cell content.

In some embodiments, assessing the health state of the lactating mammal comprises determining whether the lactating mammal is likely to be in ketosis.

In some embodiments, assessing the health state of the lactating mammal comprises estimating the progesterone levels of the lactating mammal.

In accordance with another broad aspect, there is provided a system for assessing a health state of a lactating mammal. The system comprises a light source configured for directing a light beam toward a sample of milk obtained from the lactating mammal; an imaging device configured to collect scattering data resulting from an interaction between the light beam and the sample of milk; and a processing system. The processing system is communicatively coupled to the imaging device for: processing the scattering data to determine at least one characteristic of the sample of milk; and assessing, based on the at least one characteristic of the sample of milk, the health state of the lactating mammal.

In some embodiments, the scattering data is indicative of light from the light beam being scattered along at least a first scattering angle greater than 0.5°.

In some embodiments, the light beam comprises light of at least a first wavelength and a second wavelength.

In some embodiments, the scattering data is indicative of light from the light beam being scattered along at least a first scattering angle associated with the first wavelength and of light from the light beam being scattered along a second scattering angle associated with the second wavelength, wherein the scattering data comprises a plurality of data sets each associated with a respective scattering angle.

In some embodiments, processing the scattering data comprises comparing the scattering data with angular profiles of reference milk samples having known characteristics.

In some embodiments, processing the scattering data comprises comparing the standard deviation of pixel intensity for a set of scattering profiles against the standard deviation of pixel intensity for a previous set of scattering profiles.

In some embodiments, the processing system implements a neural network, wherein processing the scattering data comprises processing the scattering data using the neural network.

In some embodiments, the processing system is further coupled to the imaging device for training the neural network using reference milk samples having known characteristics.

In some embodiments, the at least one characteristic of the sample of milk comprises at least one of a fat content, a fat-to-protein ratio, an antibiotic content, a blood content, and a somatic cell content.

In some embodiments, assessing the health state of the lactating mammal comprises determining whether the lactating mammal is likely to be in ketosis.

In some embodiments, assessing the health state of the lactating mammal comprises estimating the progesterone levels of the lactating mammal.

In accordance with another broad aspect, there is provided a method for detecting the presence of irregularities in milk. A sample of the milk is illuminated with a beam of light. Scattering data resulting from an interaction between the light beam and the sample of milk is collected. The scattering data is processed to detect the presence or absence of light scattered at a predetermined angle relative to a normal orientation. Based on the presence or absence of light, a determination is made regarding whether the irregularities are present in the sample of milk.

In some embodiments, the scattering data is indicative of light from the light beam being scattered along at least a first scattering angle greater than 0.5°.

In some embodiments, processing the scattering data comprises comparing the standard deviation of pixel intensity for a subsequent set of scattering frames against the standard deviation of pixel intensity for a previous set of scattering frames.

In some embodiments, the method further comprises sequentially capturing a plurality of scattering frames, wherein the previous set of scattering frames comprises the plurality of scattering frames.

In some embodiments, the method further comprises: capturing a subsequent scattering frame; removing an earliest one of the scattering frames from the previous set of scattering frames; and adding the subsequent scattering frame to the previous set of scattering frames to form the subsequent set of scattering frames.

In some embodiments, processing the scattering data comprises processing the scattering data using a neural network.

In some embodiments, the method further comprises training the neural network using reference milk samples having known characteristics.

In some embodiments, determining whether the irregularities are present in the sample of milk comprises determining whether white blood cells are present in the milk.

In some embodiments, determining whether the irregularities are present in the sample of milk comprises determining whether antibiotics are present in the milk.

In some embodiments, determining whether the irregularities are present in the sample of milk comprises determining a level of progesterone present in the milk.

In accordance with another broad aspect, there is provided a system for detecting the presence of irregularities in milk, comprising: a light source configured for directing a light beam toward a sample of the milk; an imaging device configured to collect scattering data resulting from an interaction between the light beam and the sample of milk; and a processing system communicatively coupled to the imaging device for: processing the scattering data to detect the presence or absence of light scattered at a predetermined angle relative to a normal orientation; and determining, based on the presence or absence of light, whether the irregularities are present in the sample of milk.

In some embodiments, the scattering data is indicative of light from the light beam being scattered along at least a first scattering angle greater than 0.5°.

In some embodiments, processing the scattering data comprises comparing the standard deviation of pixel intensity for a subsequent set of scattering frames against the standard deviation of pixel intensity for a previous set of scattering frames.

In some embodiments, the imaging device is further configured for sequentially capturing a plurality of scattering frames, wherein the previous set of scattering frames comprises the plurality of scattering frames.

In some embodiments, wherein the imaging device is further configured for: capturing a subsequent scattering frame; and wherein the processing system is further configured for: removing an earliest one of the scattering frames from the previous set of scattering frames; and adding the subsequent scattering frame to the previous set of scattering frames to form the subsequent set of scattering frames.

In some embodiments, processing the scattering data comprises processing the scattering data using a neural network.

In some embodiments, the processing system is further configured for training the neural network using reference milk samples having known characteristics.

In some embodiments, determining whether the irregularities are present in the sample of milk comprises determining whether white blood cells are present in the milk.

In some embodiments, determining whether the irregularities are present in the sample of milk comprises determining whether antibiotics are present in the milk.

In some embodiments, determining whether the irregularities are present in the sample of milk comprises determining a level of progesterone present in the milk.

In accordance with another broad aspect, there is provided a method for analyzing a composition of a fluid, comprising: illuminating, with a light beam, a sample of the fluid; collecting scattering data resulting from an interaction between the light beam and the sample of fluid; processing the scattering data to identify a light-scattering pattern produced by the interaction, the light-scattering pattern indicative of light scattered relative to a normal orientation; and analyzing the composition of the fluid based on the scattering pattern.

In some embodiments, the scattering data is indicative of light from the light beam being scattered along at least a first scattering angle greater than 0.5°.

In some embodiments, processing the scattering data comprises comparing the standard deviation of pixel intensity for a subsequent set of scattering frames against the standard deviation of pixel intensity for a previous set of scattering frames.

In some embodiments, the method further comprises sequentially capturing a plurality of scattering frames, wherein the previous set of scattering frames comprises the plurality of scattering frames.

In some embodiments, the method further comprises: capturing a subsequent scattering frame; removing an earliest one of the scattering frames from the previous set of scattering frames; and adding the subsequent scattering frame to the previous set of scattering frames to form the subsequent set of scattering frames.

In some embodiments, processing the scattering data comprises processing the scattering data using a neural network.

In some embodiments, the method further comprises training the neural network using reference milk samples having known characteristics.

In some embodiments, analyzing the composition of the fluid comprises determining whether a predetermined substance is present in the fluid.

In some embodiments, determining whether the predetermined substance is present in the fluid comprises determining whether the predetermined substance is dissolved in the fluid.

In some embodiments, the predetermined substance is one of an antibiotic, a hormone, a protein, and a fat.

In accordance with another broad aspect, there is provided a system for analyzing a composition of a fluid, comprising: a light source configured for directing a light beam toward a sample of the fluid; an imaging device configured to collect scattering data resulting from an interaction between the light beam and the sample of fluid; and a processing system communicatively coupled to the imaging device for: processing the scattering data to identify a light-scattering pattern produced by the interaction, the light-scattering pattern indicative of light scattered relative to a normal orientation; and analyzing the composition of the fluid based on the scattering pattern.

In some embodiments, the scattering data is indicative of light from the light beam being scattered along at least a first scattering angle greater than 0.5°.

In some embodiments, processing the scattering data comprises comparing the standard deviation of pixel intensity for a subsequent set of scattering frames against the standard deviation of pixel intensity for a previous set of scattering frames.

In some embodiments, the imaging device is further configured for sequentially capturing a plurality of scattering frames, wherein the previous set of scattering frames comprises the plurality of scattering frames.

In some embodiments, the imaging device is further configured for: capturing a subsequent scattering frame; and wherein the processing system is further configured for: removing an earliest one of the scattering frames from the previous set of scattering frames; and adding the subsequent scattering frame to the previous set of scattering frames to form the subsequent set of scattering frames.

In some embodiments, processing the scattering data comprises processing the scattering data using a neural network.

In some embodiments, the processing system is further configured for training the neural network using reference milk samples having known characteristics.

In some embodiments, analyzing the composition of the fluid comprises determining whether a predetermined substance is present in the fluid.

In some embodiments, determining whether the predetermined substance is present in the fluid comprises determining whether the predetermined substance is dissolved in the fluid.

In some embodiments, the predetermined substance is one of an antibiotic, a hormone, a protein, and a fat.

In accordance with another broad aspect, there is provided a method for determining a light-scattering pattern associated with the presence of a predetermined substance in a predetermined fluid, comprising: obtaining a sample of the predetermined fluid containing a predetermined quantity of the predetermined substance; illuminating, with a first light beam, the first sample of fluid; collecting scattering data resulting from a first interaction between the first light beam and the sample of fluid; processing the scattering data to identify a light-scattering pattern produced by the first interaction, the light-scattering pattern indicative of light scattered relative to a normal orientation; comparing the light-scattering pattern to a reference light-scattering pattern to determine differences therebetween, wherein the reference light-scattering pattern is produced by a second interaction between a second light beam and a reference sample of the fluid known not to contain the predetermined substance; and associating at least some of the differences between the light-scattering pattern and the reference light-scattering pattern to the predetermined substance.

In some embodiments, the scattering data is indicative of light from the first light beam being scattered along at least a first scattering angle greater than 0.5°.

In some embodiments, processing the scattering data comprises establishing a standard deviation of pixel intensity for a set of scattering frames.

In some embodiments, the method further comprises sequentially capturing a plurality of scattering frames, wherein the set of scattering frames comprises the plurality of scattering frames.

In some embodiments, the differences comprises differences between the standard deviation of pixel intensity for the set of scattering frames and a reference standard deviation associated with the reference light-scattering pattern.

In some embodiments, processing the scattering data comprises processing the scattering data using a neural network.

In some embodiments, comparing the light-scattering pattern to a reference light-scattering pattern to determine differences therebetween comprises using a neural network to compare the light-scattering pattern to a reference light-scattering pattern.

In some embodiments, the method further comprises training the neural network using the reference light-scattering pattern.

In some embodiments, the predetermined substance is dissolved in the predetermined fluid.

In some embodiments, the predetermined substance is one of an antibiotic, a hormone, a protein, and a fat.

In accordance with a further broad aspect, there is provided a system for determining a light-scattering pattern associated with the presence of a predetermined substance in a predetermined fluid, comprising: a light source configured for directing a first light beam toward a sample of the fluid; an imaging device configured to collect scattering data resulting from a first interaction between the first light beam and the sample of fluid; and a processing system communicatively coupled to the imaging device for: processing the scattering data to identify a light-scattering pattern produced by the interaction, the light-scattering pattern indicative of light scattered relative to a normal orientation; comparing the light-scattering pattern to a reference light-scattering pattern to determine differences therebetween, wherein the reference light-scattering pattern is produced by a second interaction between a second light beam and a reference sample of the fluid known not to contain the predetermined substance; and associating at least some of the differences between the light-scattering pattern and the reference light-scattering pattern to the predetermined substance.

In some embodiments, the scattering data is indicative of light from the first light beam being scattered along at least a first scattering angle greater than 0.5°.

In some embodiments, processing the scattering data comprises establishing a standard deviation of pixel intensity for a set of scattering frames.

In some embodiments, the imaging device is further configured for sequentially capturing a plurality of scattering frames, wherein the set of scattering frames comprises the plurality of scattering frames.

In some embodiments, the differences comprises differences between the standard deviation of pixel intensity for the set of scattering frames and a reference standard deviation associated with the reference light-scattering pattern.

In some embodiments, processing the scattering data comprises processing the scattering data using a neural network.

In some embodiments, comparing the light-scattering pattern to a reference light-scattering pattern to determine differences therebetween comprises using a neural network to compare the light-scattering pattern to a reference light-scattering pattern.

In some embodiments, the processing system is further configured for training the neural network using the reference light-scattering pattern.

In some embodiments, the predetermined substance is dissolved in the predetermined fluid.

In some embodiments, the predetermined substance is one of an antibiotic, a hormone, a protein, and a fat.

BRIEF DESCRIPTION OF THE DRAWINGS

The invention will be described in greater detail with reference to the accompanying drawings, in which.

DETAILED DESCRIPTION

The collection of milk from lactating mammals has a long history, given the lauded nutritional properties of milk. Now, modern techniques for collecting milk from lactating mammals are highly mechanized and automated. The lactating mammal, which may be a cow, a goat, a sheep, or any other suitable mammal, enters a designated milking station and a mechanical apparatus is connected to the udder and/or teats of the mammal for extraction of milk. The collected milk is then sent to a milk processing facility where the milk may be tested, filtered, purified, or otherwise treated to be ready for consumption or used for making other products.

Figure 1:
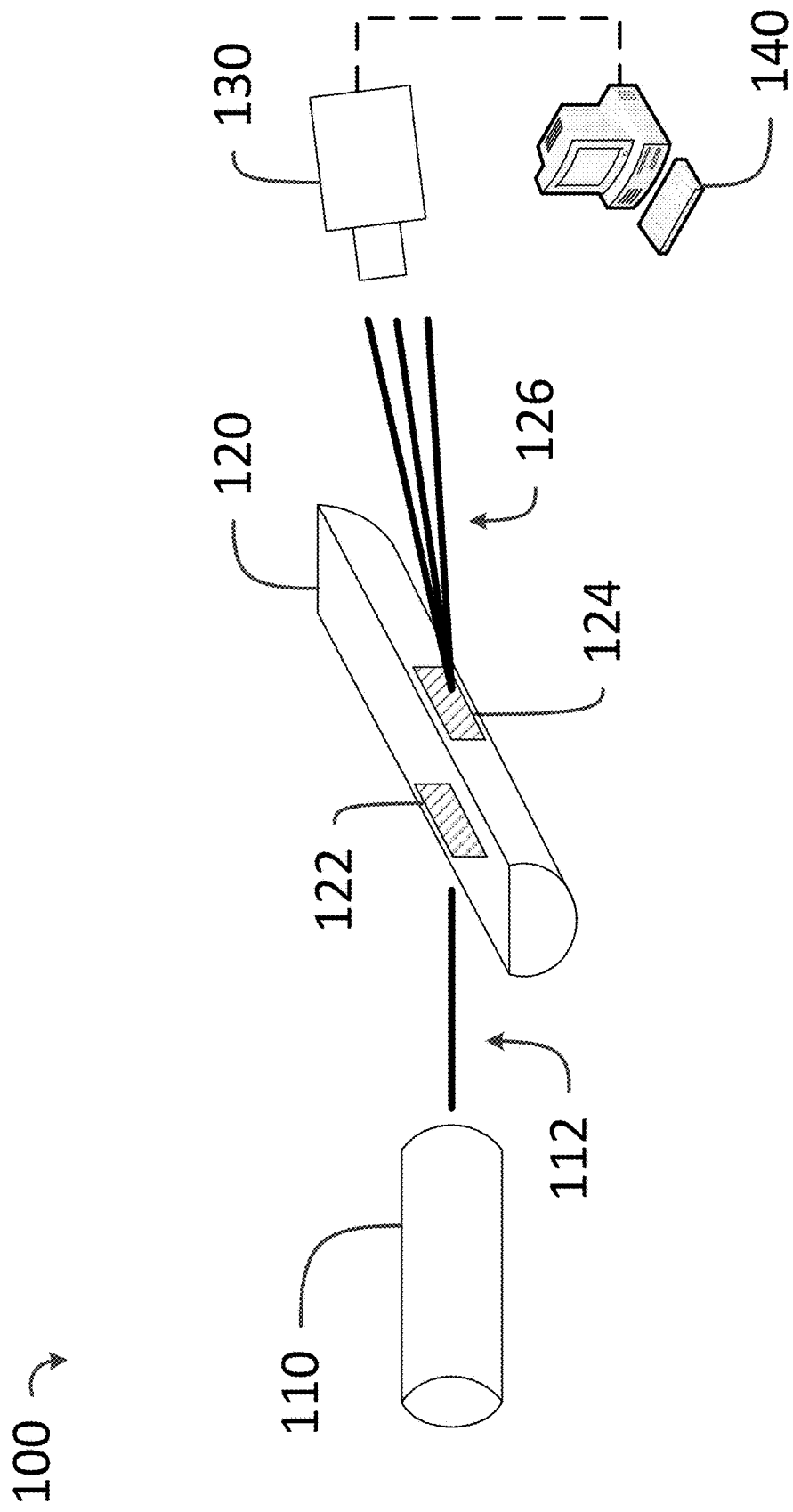
FIG. 1 is a schematic diagram of a light-scattering milk analysis system.

With reference to FIG. 1, a light-scattering detection system 100 for testing milk obtained from a lactating mammal is shown. The light-scattering detection system 100 may be used to evaluate various characteristics of milk obtained from a lactating mammal, to assess the quality of the milk, and/or to assess a health state of the lactating mammal which produced the milk. The light-scattering detection system 100 includes a light source 110, a sample container 120, an imaging device 130, and optionally a computing device 140. It should be noted that the milk used in conjunction with the light-scattering detection system 100, as detailed hereinbelow, may be collected from a single lactating mammal, or from a group of lactating mammals, for example when milk from multiple lactating mammals is pooled for processing. The light-scattering detection system can be attached in-line to conventional milking systems in dairy barns or facilities where milking takes place.

The light source 110 is configured to illuminate a sample of milk held in the sample container 120 with a light beam 112. In some embodiments, illuminating the sample of milk with the light beam 112 includes directing light produced by the light source 110 as a central ray of light at the sample of milk, for example by using a collimating lens. The light source 110 may be a source of laser light or of diffuse light, as appropriate, and may use a collimating lens to produce a central ray of light, as appropriate. The light beam 112 produced by the light source 110 may be of substantially a single wavelength, or may include light of a plurality of wavelengths. In some embodiments, the light source 110 produces a light beam 112 which includes light having a wavelength of approximately 780 nm, although other wavelengths may be used. In some embodiments, multiple light sources 110 are used, for example with each one of the light sources 110 producing a respective light beam 112 having a distinct wavelength. In some embodiments, the light source 110 also includes a stand or other supporting structure for supporting the light source 110.

The sample container 120 serves to receive and, in some embodiments, hold a sample of milk produced by the lactating mammal which is used to perform scattered-light-based measurements. In some embodiments, the sample container 120 is connected to a larger milk collection system and is provided with the sample of milk from one or more lactating mammals by the milk collection system via one or more tubes or other conduits. The sample container 120 may be cylindrical, oval, or take on any other suitable shape. In some embodiments, the sample container 120 is further connected to the milk collection system for returning the sample of milk after testing has been performed on the sample of milk, for example to a reservoir or other holding tank. In some other embodiments, the sample container 120 is configured to allow milk to flow through in a substantively continuous fashion, and the sample of milk used for testing is any milk present in the sample container 120 at a time when a test is performed. A diverter can be incorporated for separating milk on the basis of desired physical parameters, such as fat content and characteristics such as low somatic cells, or other desired characteristics. For instance, the diverter can be positioned at an output end of the sample container 120 for separating milk after the analysis is performed at the sample container 120. In some embodiments, the sample container is a component of a milking line in the processing system. In other components, the sample container 120 is embodied in a portable device which can be carried, along with the light source 110, the imaging device 130, and optionally the computing device 140 for use at remote locations, on a milk transport system taking the milk from a producer to a milk processor, or separate from the milk collection system. In still further embodiments, the light-scattering detection system 100 may be implemented in a laboratory setting or even at a milk processing facility for quality assurances or other purposes before the milk from a producer is processed.

In order to illuminate the sample of milk in the sample container 120, the light source 110 and the sample container 120 are positioned to direct the light beam 112 from the light source 110 toward the sample container 120, for example toward an input view port 122 of the sample container 120. The input view port 122 may be an opening or other aperture produced in the sample container 120 and sealed with a transparent or otherwise light-permitting material, for instance glass, plastic, and the like.

The sample container 120 also has an output view port 124 through which forward-scattered light 126 is allowed to propagate and can be detected. The output view port 124 may be substantively similar to the input view port 122. In some embodiments, a field of view of the output view port 124 is wider than a field of view of the input view port 122. The forward-scattered light 126 results from interactions between the light beam 112, which enters the sample container 120 via the input view port 122, and the milk in the sample container 120. When the light beam 112 comes into contact with the milk in the sample container 120, some or all of the light is scattered by the milk. Depending on the wavelength of the light in the light beam 112, the amount of scattered light, and the angle at which the light is scattered, may be indicative of the presence or absence of particular molecules and/or cells in the milk. In some embodiments, the light source 110 and the viewing ports 122 and 124 are implemented using fiber optics and one or more microelectromechanical systems (MEMS), which may be located inside the sample container 120, In this context, light scattering is caused by the interaction of the oscillating dipole of the light source with the dipoles within the particles that make up the substance. This interaction results in secondary excitation of dipoles, causing the scattering phenomena. Most of the detection of particles relies on the particles having a size and a distinct polarizability due to differences in the dipoles within the particles. Larger sized particles, such as somatic cells in the milk can be detected at narrow forward scattering angles (as described by U.S. Pat. No. 9,389,175, which is incorporated herein by reference in its entirety). However, the detection of dissolved particles such as antibiotics, hormones, or the like, can require further processing of the scattering data using various mathematical techniques, as discussed in greater detail hereinbelow. For example, mathematical techniques involving either an image or a sequence of images, edge detection methods associated with image processing, standard deviation of parts within a sequence of images, or other digital filters for finding specific features, can be employed. In some embodiments, the present disclosure can differ from previous approaches, inter alia, as it makes use different mathematical techniques to characterize a scattering measurement.

The forward-scattered light 126 is received by the imaging device 130, which is positioned in a suitable way for receiving the forward-scattered light 126 as emitted from the output view port 124. In some embodiments, the light source 110, the sample container 120, and the imaging device 130 are positioned such that the sample container 120 is located substantively between the light source 110 and the imaging device 130. In some embodiments, the imaging device 130 is configured to receive light having a forward scattering angle of more than 0.5°. For example, the imaging device 130 receives the forward-scattered light 126 which has forward scattering angles between 1° and 45°, between 0.5° and 50°, or any other suitable range. It will be appreciated that characteristics of the optical components, including the focal length of a lens on the imaging device 130, can result in numerical changes in the disclosed angles.

In some embodiments, the imaging device 130 is a digital camera using any suitable image-capturing technology. For example, the imaging device 130 is a webcam or other off-the-shelf digital camera. In one particular embodiment, a webcam with an image resolution of 1280×720 pixels and a 3.6 mm focal length lens can be used. In another example, the imaging device 130 is a wide-angle camera. The imaging device 130 is configured for collecting scattering data relating to the forward-scattered light 126. The scattering data provides a "scattering profile" for the milk, which is indicative of the way the light beam 112 is scattered by the milk to produce the forward-scattered light 126, for example based on the intensity of the forward-scattered light 126. The scattering data is based on a so-called "forward scattering angular range" for the forward-scattered light 126. That is to say, the scattering which is produced in the same direction of transmission as the light beam 112, and based on an angle of incidence of the light beam 112 on the milk in the sample container 120.

In some embodiments, the scattering data is a data array which consists of numerical data. For example, the numerical data is indicative of a grey-scale representation of the forward-scattered light 126, of a colour-coded representation of the forward-scattered light 126, and/or of any other suitable scheme that identifies the intensity, frequency, phase, or any other suitable parameter of the forward-scattered light 126 as received by the imaging device 130.

By analyzing the scattering data, for example with the computing device 140 or another processing system, which may be incorporated as part of the imaging device 130 or may be a separate entity, various characteristics about the milk in the sample container 120 may be determined. For instance, measurement of the frequency shifts, angular distribution, the polarization, and the intensity of the forward-scattered light 126 is indicative of the size, shape, and molecular interactions in the scattering material.

Traditionally, analysis of scattering data has relied on a determination of the intensity of the scattering as a function of the forward scattering angle. Mathematical means including time-dependent statistical mechanics, electrodynamic calculations, curve fitting, and statistical measures, such as concentration-dependent changes, are used to determine some characteristic of a scattering medium, for example structural features or molecular dynamics. In contrast, one approach proposed herein evaluates the standard deviation of pixel intensity in images captured by the imaging device 130. As described in greater detail hereinbelow, changes in the standard deviation of the intensity of scattered light at particular angles, or within a region of interest, can be indicative of the presence of irregular substances present as particles or dissolved in milk, and in fluids generally.

In the case of milk, it should be noted that during milking, the physical characteristics of the produced milk changes: concentrations of fat, free fatty acids, lactose, total solids, water content, and density can all vary during milking. Each of these components of the milk is associated with some aspect of health of the animal, and affects the forward-light-scattering properties of the milk.

The production of the forward-scattered light 126 results from the interaction between the light beam 112 and the sample of milk. The light beam 112 induces an oscillating polarization (or some other state of excitation) of electrons in various molecules in the milk which act as secondary sources of light, producing the scattered light 126. The scattered light can be produced by cells, parts of cells, and the like. For instance, the presence of substances such as chemicals (hormones, antibiotics) or biological agents (bacteria, foreign cells) may be indicated by the scattering data. In some embodiments, one or more of fat content, protein content, fat-to-protein ratio, somatic cell distribution, estimate of ketosis, hormone levels, such as progesterone, or the presence of antibiotics and/or blood can be determined based on analysis of the scattering data.

It should be noted that processing of the acquired data can be done on-site, i.e. where the sample of milk is obtained, or remotely using a processor capable of acquiring data, storing data for mathematical processing and interpretation, and for storing data so historical information can be available.

In addition, it should be noted that determining various characteristics of the milk from the scattering data does not require the use of additives such as dyes, emulsifying agents, chemicals or biological agents, antibodies, thermal regulation, dilution, or the like. Changes in the chemical or nutritional properties of the milk being tested are not required, leaving the sample of milk suitable for any subsequent intended use.

With reference to FIG. 2, there is shown a method 200 for assessing a health state of a lactating mammal. The method 200 may be implemented via the light-scattering detection system 100. At step 202, a sample of milk obtained from a lactating mammal, for example the sample of milk held in the sample container 120, is illuminated with a light beam, for instance the light beam 112 produced by the light source 110.

At step 204, scattering data, resulting from an interaction between the light beam 112 and the sample of milk in the sample container 120, is collected, for example via the imaging device 130. The scattering data may include any suitable information about the forward-scattered light 126 produced by the light beam 112 and the milk. The forward-scattered light 126 on which is based the scattering data may include forward-scattered light having a forward scattering angle between 0.5° and 50°. It should be noted that the angles of light-scattering are, in some embodiments, at least in part determined by the optical geometry and distances between the imaging device 130 and the sample container 120, and that the optical geometry of the light-scattering detection system 100 can be optimized for detection. The position of pixels in the scattering data collected by the imaging device 130 can be associated with the angle of scattering.

In some embodiments, a neural network or other machine-learning tool is used to process the scattering data to perform determinations about characteristics of the milk in the sample container 120 and/or about a health state of the lactating mammal. The neural network may be implemented by the imaging device 130 and/or by the computing device 140, as appropriate. In order for the neural network to process the scattering data, the neural network may need to first be trained.

Thus, optionally, at step 206, the neural network is trained using reference samples of milk having known characteristics. In some embodiments, a number of scattering profiles for samples of milk having known characteristics are used as a training set for the neural network. The known characteristics may include fat content, fat-to-protein ratio, protein content, somatic cell count, water content, antibiotic and/or blood presence, presence of water, and the like. The number of scattering profiles may be a dozen, several dozen, a hundred, several hundred, a thousand, several thousand, several tens of thousands, or any other suitable number. For example, several hundred scattering profiles for samples of milk having a known fat content are used to train the neural network. In another example, several thousand scattering profiles for samples of milk having known red and/or white blood-cell counts are used to train the neural network.

In some embodiments, the scattering profiles for samples of milk having known characteristics are used in a semi-supervised machine-learning approach with a multiple causes, multiple indicators model. In some embodiments, the neural network is aided by a heuristic model. In other embodiments, an unsupervised learning model is used. In addition, the neural network may be implemented via discrete application packages, which interface via an application programming interface (API).

At step 208, the scattering data is processed to determine at least one characteristic of the sample of milk in the sample container 120. The scattering data may be processed by the imaging device 130 itself, or by the computing device 140, where appropriate. The processing may involve various types of mathematical transformations of the image, including evaluating the standard deviation of the pixels to assess angular ranges at which the greatest changes in scattering intensities are occurring. The scattering data may be used to determine one or more of a fat content, a protein content, a fat-to-protein ratio, a somatic cell distribution, a level of progesterone, a presence of antibiotics, a presence of blood, and the like. In some embodiments, the scattering data is processed by comparing the scattering profile of the milk in the sample container 120 against a library of scattering profiles from milk samples with known characteristics. The comparison may be performed using standard computational techniques, including suitable statistical methods and best fit techniques, or using the neural network described hereinabove.

At step 210, a health state of the lactating mammal is assessed based on the at least one characteristic of the sample of milk. For example, the characteristics of the sample of milk can be used to determine whether the lactating mammal is in a state of ketosis. In another example, the presence of antibiotics, as determined at step 208, can be used to determine other health characteristics of the lactating mammal.

The health state of the lactating mammal may be assessed by the imaging device 130 and/or the computing device 140, as appropriate. In some embodiments, the neural network used at step 208, or another neural network, is used to perform the assessment of the health state of the lactating mammal. For instance, a library of health characteristics of lactating mammals having known health states is used to train the neural network to identify an unknown health state of a lactating mammal which produces milk having particular characteristics, as determined at step 208. In other embodiments, other computational techniques are used to assess the health state of the lactating mammal.

Figure 2A:
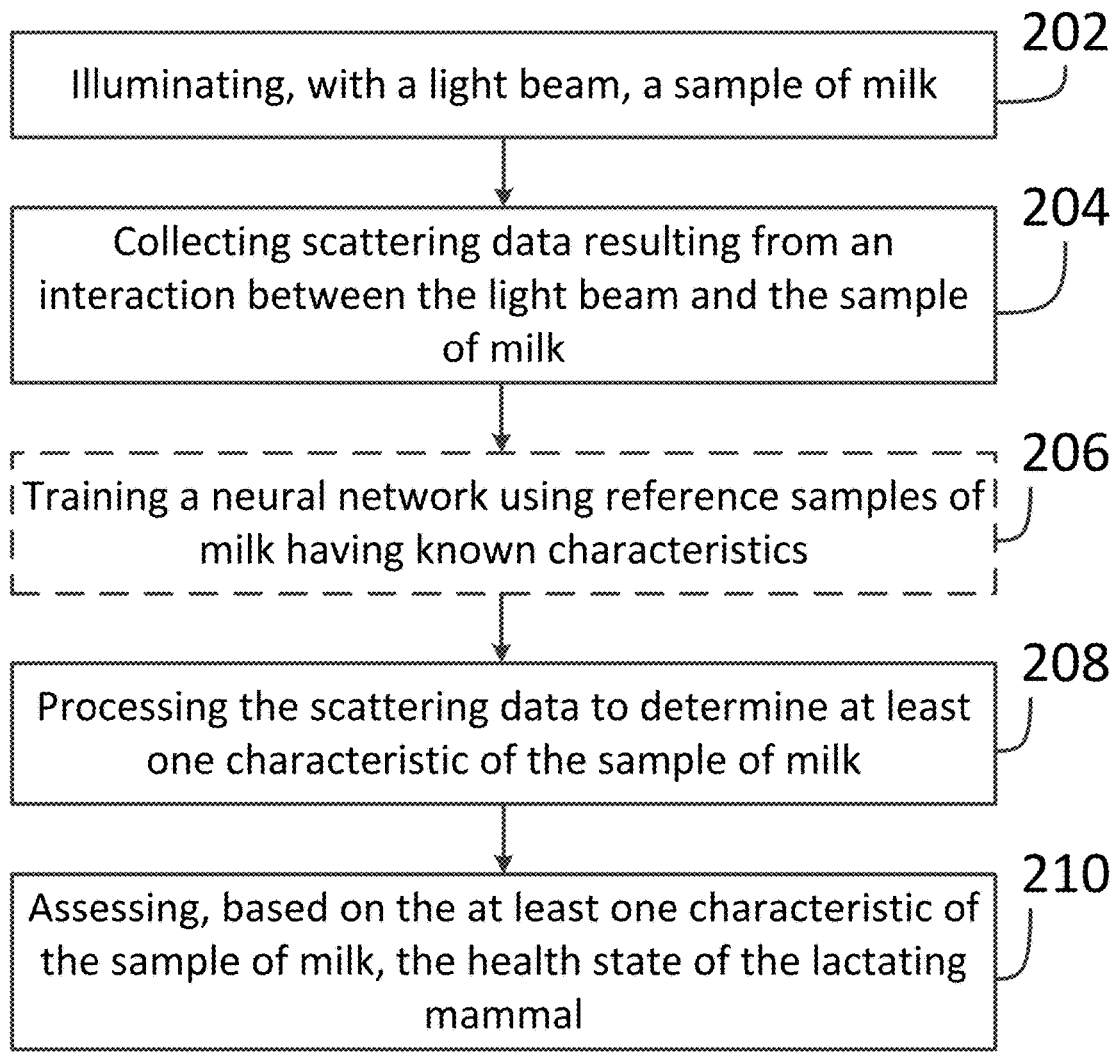
FIG. 2A is a flowchart illustrating an embodiment of a process for assessing a health attribute of a lactating mammal.
Figure 2B:
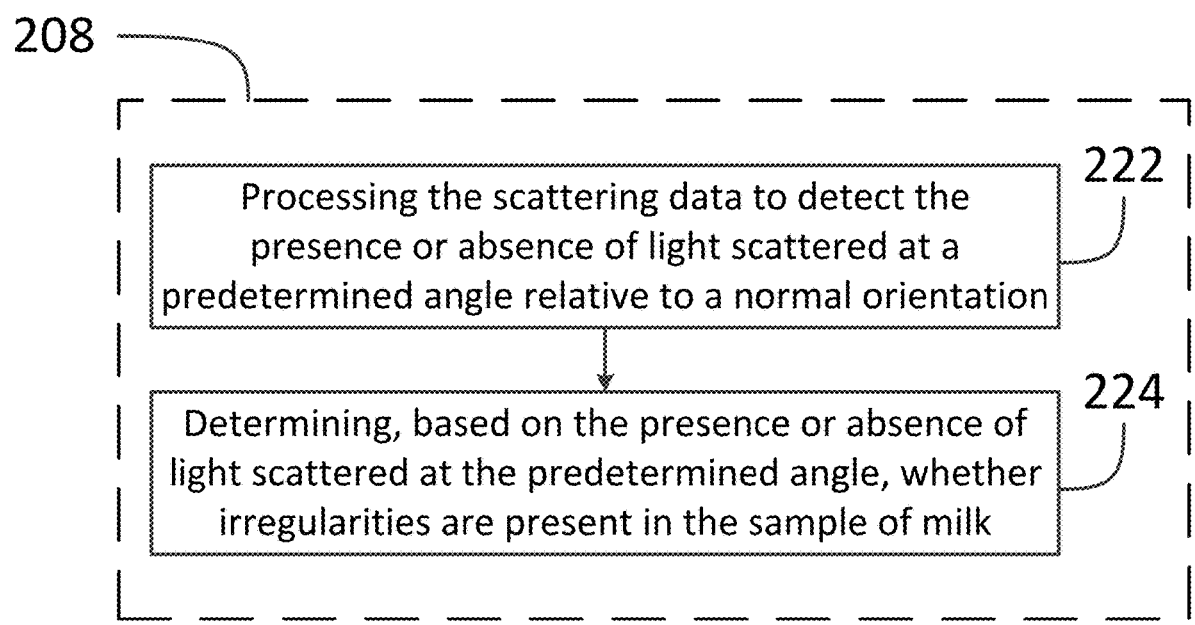
FIGS. 2B-C are flowcharts illustrating example embodiments of a step of the flowchart of FIG. 2A for determining the presence of irregularities in milk.

With additional reference to FIG. 2B, the method 200 can alternatively, or in addition, be used to determine whether irregularities are present in milk. In the present context, the term "irregularities" can refer to any one or more of blood cells, including white and red blood cells, hormones, undesirable chemicals, antibiotics, and the like, and/or biological agents, including bacteria, foreign cells, and the like. In some cases, the embodiment of step 208 illustrated in FIG. 2A is the embodiment of step 208 used as part of method 200 when used for assessing the health state of the lactating mammal. In other cases, other embodiments of step 208 can be used as part of method 200 when used for assessing the health state of the lactating mammal.

At step 222, the scattering data is processed to detect the presence, or absence, of light scattered at a predetermined angle relative to a normal orientation. The normal orientation can be any suitable orientation, for instance parallel with an angle of incidence of the light beam, with an angle of detection of the imaging device 130, or any other orientation. As the light beam interacts with the milk, various substances in the milk can cause the light to be scattered at respective angles. One or more predetermined angles can be established as being indicative of associated substances: for instance, penicillin may cause scattering at one or more angles between 2° and 8°; in another instance, progesterone may cause scattering at one or more angles between 1.5° and 9°; in a further instance, certain antibiotics may cause scattering at one or more angles between 5.5° and 16°. When detected, in some embodiments, the scattered light presents as a ring or disk, located substantially in a plane and centered about the normal orientation. In other embodiments, the scattered light is detected based on a count of received photons at particular pixels of the imaging device 130. Still other embodiments are considered. Thus, the scattering data obtained at step 204 can be processed to detect the presence or absence of light scattered at one or more of the predetermined angles associated with substances which can be present in the sample of milk.

At step 224, the presence of irregularities in the sample of milk can be determined based on the presence or absence of light scattered at the predetermine angle. For example, if, at step 222, the presence of light scattered at an angle associated with progesterone is detected, then the presence of progesterone in the sample of milk can be determined. Similarly, if the presence of light scattered at an angle associated with white blood cells is detected at step 222, the presence of white blood cells in the sample of milk can be determined.

Although the foregoing discussion relating to steps 222 and 224 were in relation to a single predetermined angle, in order to determine the presence of irregularities, it should be noted that step 222 can be performed by processing the scattering data to detect the presence or absence of light scattered at multiple predetermined angles, each of which associated with respective irregularities, in order to determine whether multiple different irregularities are present. In addition, other numerical techniques, such as principal component analysis, curve-fitting techniques, and integration can be used.

Figure 2C:
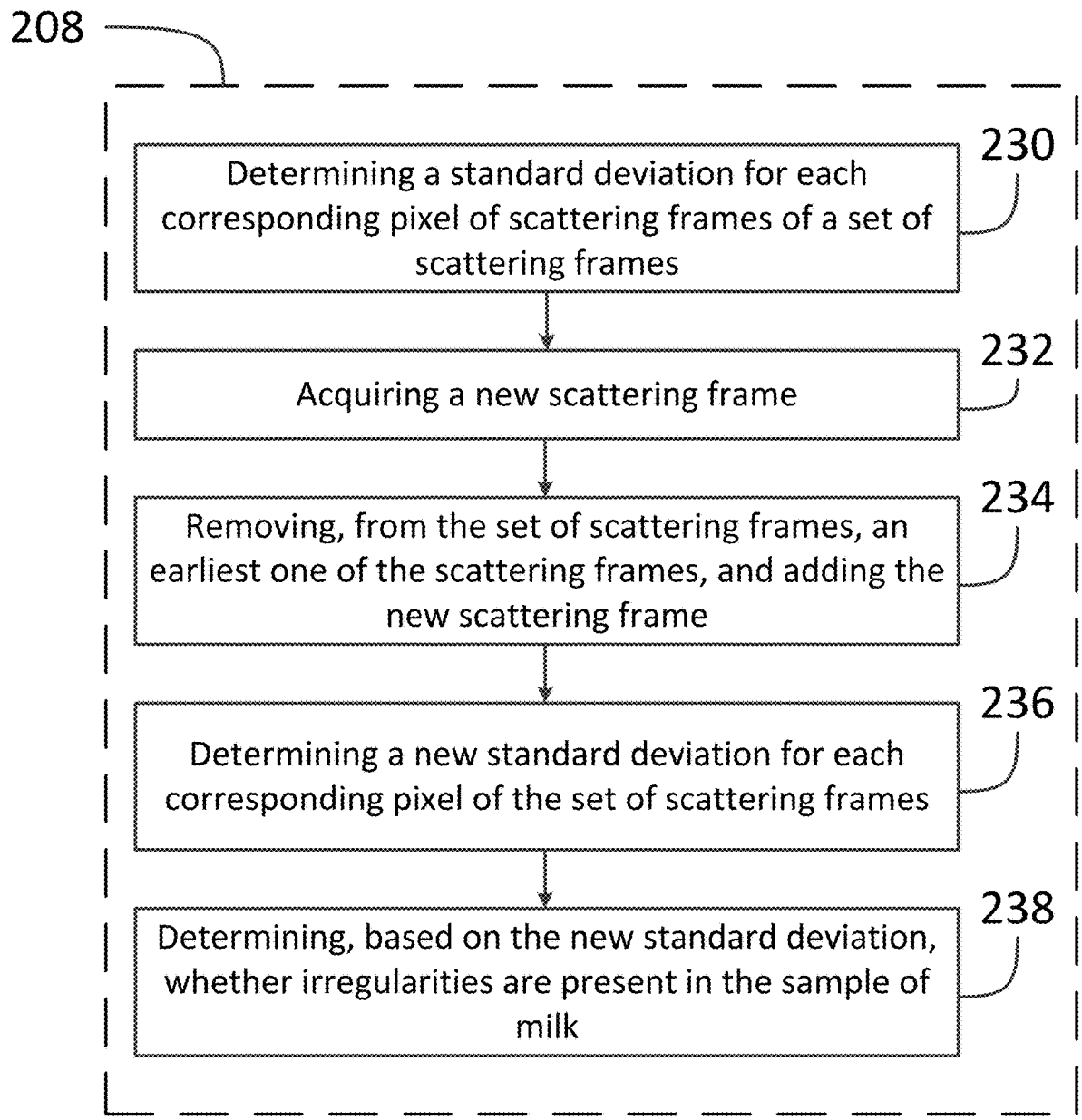

With additional reference to FIG. 2C, another embodiment of step 208 used as part of method 200 is illustrated. As part of this embodiment of step 208, a set of scattering frames is used: a scattering frame can be a snapshot of the scattering pattern produced by the operation of the light-scattering detection system 100, for instance as captured by the imaging device 130. The set of scattering frames can include any number of scattering frames; in some embodiments, 50, 100, or 200 scattering frames are used to form a set, but any other suitable number can be used. Each of the scattering frames are of substantially the same size, such that a pixel on one scattering frame corresponds to the same pixel (i.e., at the same location in the frame) in each of the other scattering frames.

At step 230, a standard deviation for each corresponding pixel of the scattering frames is determined. The standard deviation can be, for example, relative to the intensity of each corresponding pixel across the scattering frames of the set of scattering frames. For instance, the intensity values for the pixels located at point (10,10) in each of the scattering frames is evaluated to determine the standard deviation for the pixel at (10,10); similar determinations are also made for the remaining pixels in the scattering frames.

At step 232, a new scattering frame is acquired, for instance by the operation of the imaging device 130. New scattering frames can be acquired periodically, for example every few milliseconds, or every few seconds, or can be acquired in response to a trigger or event, as appropriate. At step 234, the earliest scattering frame of the set is removed, and the new scattering frame is added to the set. The earliest scattering frame can be determined, for example, based on timestamps associated with the scattering frames. By removing the earliest scattering frame and adding the newest one, the total number of scattering frames in the set is kept constant.

At step 236, a new standard deviation is calculated for the set of scattering frames, including the new scattering frame. Substantially similar operations may be performed. At step 238, based on the new standard deviation, a determination is made regarding whether irregularities are present in the sample of milk. For example, the particular changes in the standard deviations of specific pixels can be indicative of the presence of one or more irregularities in the sample of milk.

In some embodiments, the previous standard deviation is compared against the new standard deviation on a pixel-by-pixel basis, and changes in the standard deviation which exceed a particular threshold can be used as an indication of the presence of particular irregularities in the sample of milk. In other embodiments, steps 230 to 238 are repeated iteratively, and changes in the standard deviation over multiple iterations is used as an indication of the presence of particular irregularities in the sample of milk. Still other embodiments are considered.

Figures 3A, 3B:
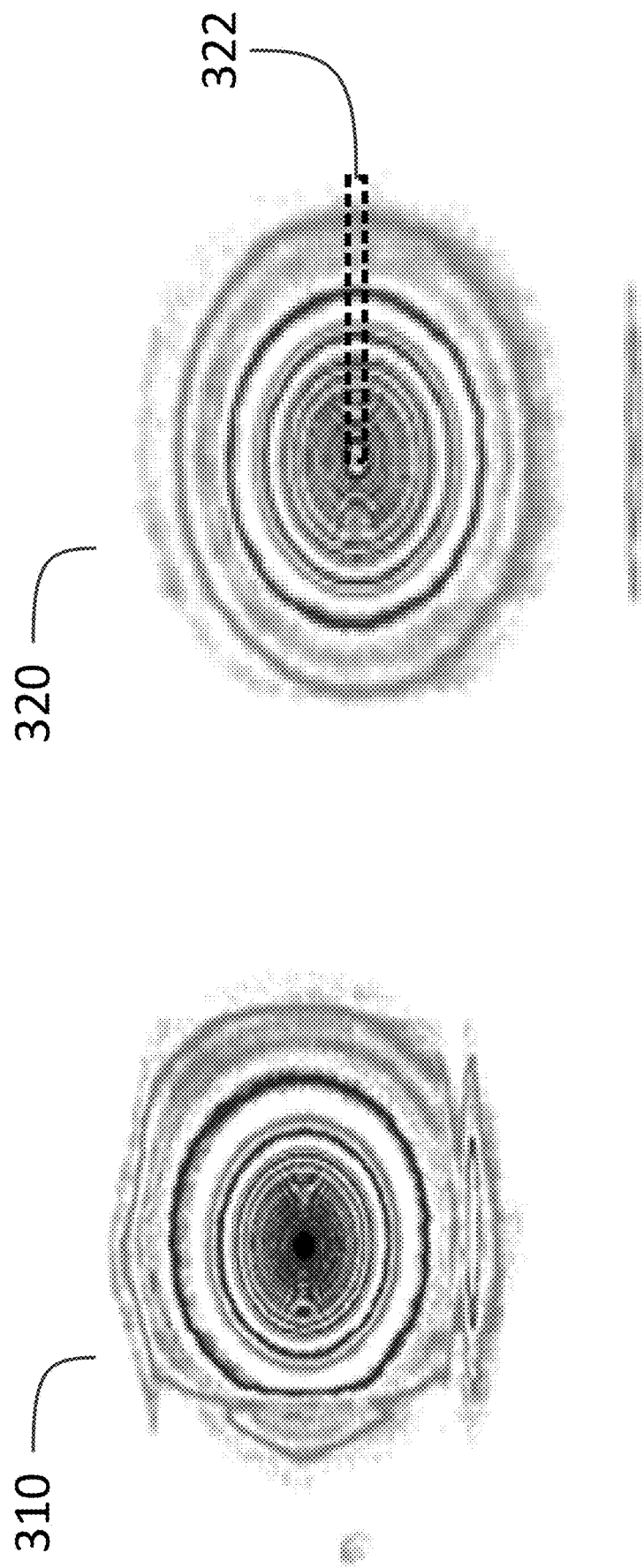
FIGS. 3A-B are illustrations of example scattering frames.

With reference to FIGS. 3A-B, in some embodiments, processing the scattering data is performed by selecting, from the totality of the scattering data, a region of interest. FIG. 3A illustrates a scattering frame 310 for raw milk, and FIG. 3B illustrates a scattering frame 320 for milk which contains an irregular substance. In order to analyze the scattering frame 320, a region of interest 322 can be selected. The region of interest can extend substantially from a centre point of the scattering data, which corresponds substantially with the normal orientation, to an outer edge of the scattering data.

Figure 4:
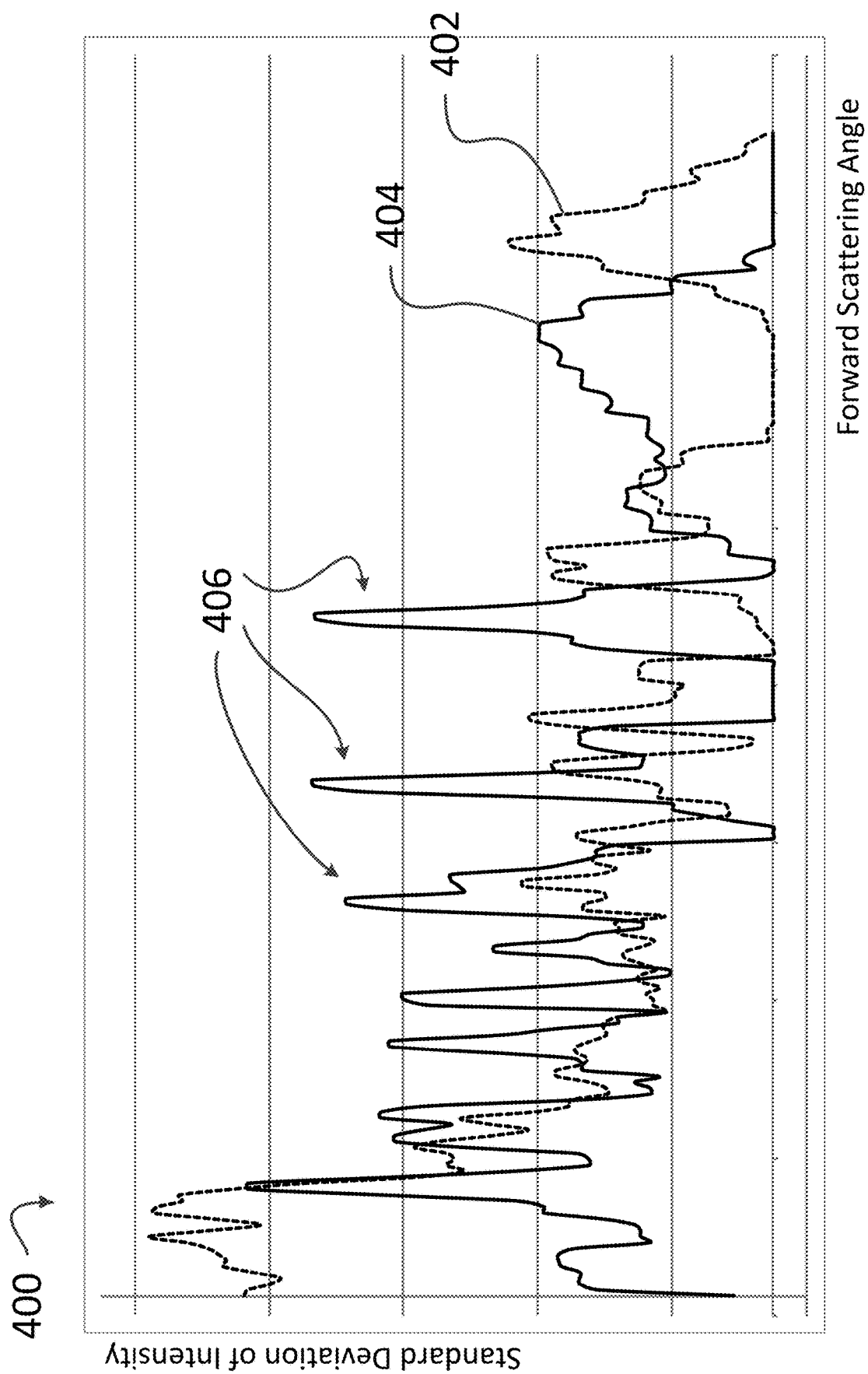
FIG. 4 is a graphical representation of scattering data.

With reference to FIG. 4, the scattering data found in the region of interest, for instance over an entire set of scattering frames, can be evaluated to identify standard densities of intensity of the scattered light relative to the forward scattering angle, for example as plotted in the graph 400, in which the standard deviation of intensity for raw milk is shown in dotted line 402, and the standard deviation of intensity for milk with the irregular substance is shown in line 404. Graph 400 can be used to determine the presence of irregularities: for example, the angles at which there exists scattered light when the irregular substance is present, but not in raw milk, can be used as a signature for the particular substance. For instance, any one or more of peaks 406 could be used as the signature for the irregular substance. As described in greater detail hereinbelow, a procedure for determining appropriate signatures for various substances can be developed.

Although the preceding discussion focused primarily on lactating mammals which are domesticated animals, including cows, goats, and sheep, it should be noted that similar techniques as those described herein are applicable to human milk. Milk collecting from a lactating human may be illuminated with one or more light beams and forward-scattered light resulting from the interactions between the light beams and the human milk may be collected and analyzed to assess one or more health attributes of the lactating human.

Figure 5:
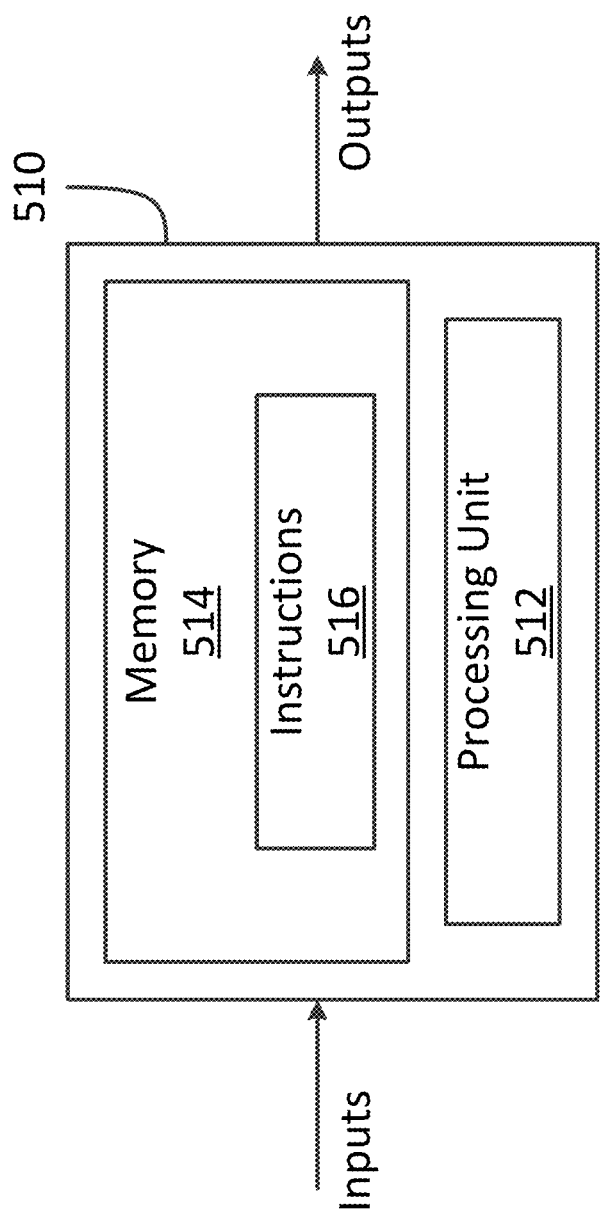
FIG. 5 is a schematic diagram of an embodiment of a computing system for implementing the method of FIG. 2 in accordance with an embodiment described herein.

With reference to FIG. 5, the method 200 may be implemented by a computing device 510, comprising a processing unit 512 and a memory 514 which has stored therein computer-executable instructions 516. Embodiments of the computing device 510 include the computing devices 102, 104, and 106 described hereinabove.

The processing unit 512 may comprise any suitable devices configured to implement the method 200 such that instructions 516, when executed by the computing device 510 or other programmable apparatus, may cause the functions/acts/steps of the method 200 described herein to be executed. The processing unit 512 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 514 may comprise any suitable known or other machine-readable storage medium. The memory 514 may comprise non-transitory computer readable storage medium, for example, but not limited to, an electronic, magnetic, optical, electromagnetic, infrared, or semiconductor system, apparatus, or device, or any suitable combination of the foregoing. The memory 514 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 514 may comprise any storage means (e.g., devices) suitable for retrievably storing machine-readable instructions 516 executable by processing unit 512. In some embodiments, the memory 514 can also be used to store various information, including reference information and the like, as discussed in greater detail hereinbelow, which may be used during implementation of the method 200, or of other methods disclosed herein.

With reference to FIG. 4, the computing device 510 is configured for implementing a health state assessment (HSA) system 600. The HSA system 600 is configured for receiving forward-scattered light, for example forward-scattered light 126, resulting from an interaction between a light beam, for example the light beam 112 produced by the light source 110, and a sample of milk, for example the sample of milk held in the sample container 120. The light source 110 illuminates the sample of milk in the sample container 120 with the light beam 112, as per step 202. The HSA system 600 includes a light collector 610, a scattering analysis module 620, a milk characteristic module 630, and a classification module 640.

The light collector 610 is configured for receiving the forward-scattered light 126 resulting from the interaction between the light beam 112 and the sample of milk. The light collector may include one or more digital cameras, for example a webcam or other off-the-shelf camera. The light collector 610 is communicatively coupled to the scattering analysis module 620 to provide the scattering analysis module 620 with information regarding the forward-scattered light 126. It should be noted that in some embodiments, the light collector 610 is a component of the scattering analysis module 620.

The scattering analysis module 620 is configured to collect light-scattering data based on the forward-scattered light 126, which results from the interaction between the light beam 112 and the sample of milk, as per step 204. The scattering analysis module 620 is configured to collect any suitable light-scattering data, including light intensity, light frequency, light phase, and the like. In some embodiments, the scattering analysis module 620 collects the light-scattering data in the form of one or more arrays of data. The scattering analysis module 620 is configured for providing the light-scattering data to the milk characteristic module 630.

The milk characteristic module 630 is configured for processing the light-scattering data obtained from the scattering analysis module 620 to determine at least one characteristic of the sample of milk, as per step 208. For example, the milk characteristic module 630 determines one or more of a fat content, a protein content, a fat-to-protein ratio, a somatic cell distribution, a level of progesterone, the presence of antibiotics and/or blood, and the like. In some embodiments, the milk characteristic module 630 has access to a database 632 which stores a library of scattering profiles from milk samples with known characteristics against which the scattering profile of the milk in the sample container 120 is compared. In some other embodiments, the milk characteristic module 630 implements a neural network for comparing the scattering profile of the milk in the sample container against the library of scattering profiles from milk samples with known characteristics. In some embodiments, the neural network implemented by the milk characteristic module 630 uses the library of scattering profiles from milk samples with known characteristics in the database 632 as a training set, as described in step 206. In some embodiments, each of the characteristics being determined about the sample of milk is associated with a respective library of scattering profiles. The milk characteristic module 630 is configured for providing the characteristics of the sample of milk to the health state module 640.

The health state module 640 is configured for assessing, based on the milk characteristics obtained from the milk characteristic module 630, a health state of the lactating mammal which produced the milk sample held in the sample container 120. In some embodiments, the neural network implemented by the milk characteristic module 630, or another neural network, is used to assess the health state of the lactating mammal. The neural network used to assess the health state of the lactating mammal may be trained based on a data set found in the database 632. In other embodiments, other computational techniques are used to assess the health state of the lactating mammal.

In some embodiments, the health state module 640 uses a variety of predictive classification models (PCMs) to assess the health state of the lactating mammal. For example, the health state module 640 uses a progesterone PCM to assess high, low, and medium levels of progesterone in the lactating mammal. In another example, the health state module 640 uses a fat PCM to assess a fat content of the milk produced by the lactating mammal, which may then be used to bin the mammal into one or more health states. In a further example, the health state module 640 uses an antibiotics PCM to assess the presence or absence of antibiotics in the milk produced by the lactating mammal, which may then be used to assess a health state of the lactating mammal. In a still further example, the health state module 640 uses a nutritional health PCM to assess a nutritional health of the lactating mammal, which may then be used to assess whether the lactating mammal is in ketosis.

For instance, the presence of progesterone (sometimes called P4) in milk can be an indicator of reproductive status of the lactating mammal. In some cases, cows which are not pregnant beyond a 90 day post-calving period will produce lower quantities of milk, which can result in financial losses. Thus, the health state module 640 can use the progesterone PCM to warn a milk producer of potential problems related to the progesterone levels of a particular cow. In addition, the health state module 640 can use the progesterone PCM to inform a milk producer regarding whether or not a previously-inseminated cow is pregnant or not.

It should be noted that the principles described herein may also be used to detect abnormalities with a milk collecting system. For example, a particular scattering profile may be indicative of cleaning products or other undesirable elements being present in the milk held in the sample container 120. An approach similar to that disclosed in the method 200 may thus be used to evaluate a health state of a milk processing plant, for example to locate issues with cleaning systems or infiltration of undesirable substances, to evaluate whether certain regulatory cleaning steps have been successfully undertaken, and/or to evaluate whether acid wash and detergent wash cycles have been successfully completed in an appropriate order and for an appropriate cleaning duration.

In addition, in some embodiments, one or more of the light collector 610, the scattering analysis module 620, the milk characteristic module 630, and the health state module 640 can be combined or further subdivided, as appropriate. For example, the scattering analysis module 620, the milk characteristic module 630, and the health state module 640 can all be implemented as a single module.

In some embodiments, the HSA system 600 can be configured to evaluate only scattered light at certain predetermined scattering angles, for example light-scattering angles associated with the presence of irregularities and/or particular substances in milk. This approach may, for example, allow for the use of lower-capability processing systems and/or reduced hardware requirements.

With reference to FIG. 5, the techniques disclosed herein can be used to analyze the composition of a fluid, which can be milk, as disclosed hereinabove, or another suitably translucent fluid, in accordance with a method 700. At step 702, a sample of the fluid is illuminated with a light beam. At step 704, light-scattering data resulting from an interaction between the light beam and the sample of fluid is collected. A setup substantially similar to the light-scattering detection system 100 shown in FIG. 1 could be used.

At step 706, the light-scattering data is processed to identify a light-scattering pattern produced by the interaction. At step 708, the composition of the fluid is analyzed based on the light-scattering pattern. The processing and analysis steps can substantially mirror those presented in the method 200. For instance, depending on the particular scattering angles produced by the interaction between the fluid sample and the light beam, various determinations about the presence of one or more substances in the fluid can be made.

Figure 6:
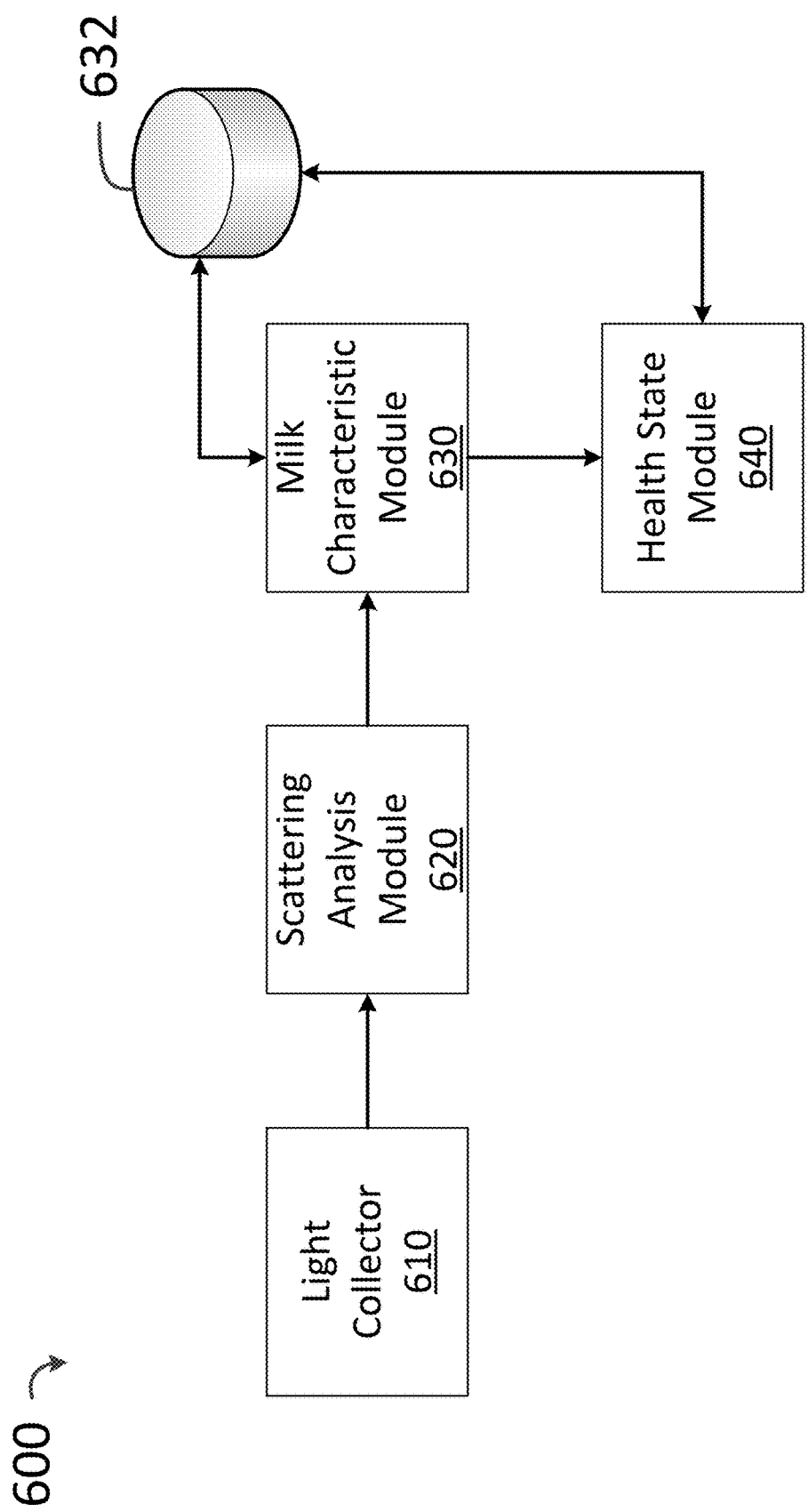
FIG. 6 is a block diagram of an example system for assessing a health attribute of a lactating mammal.
Figure 7:
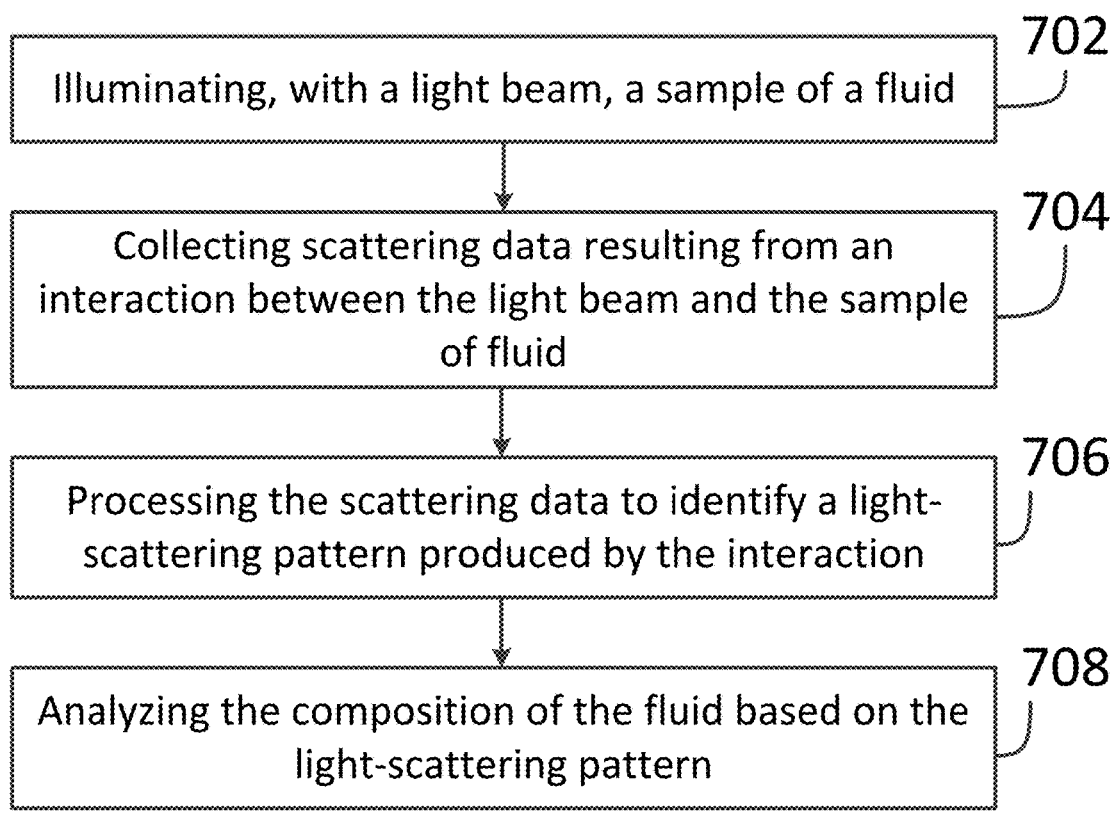
FIG. 7 is a flowchart illustrating an embodiment of a process for analyzing a composition of a fluid.
Figure 8:
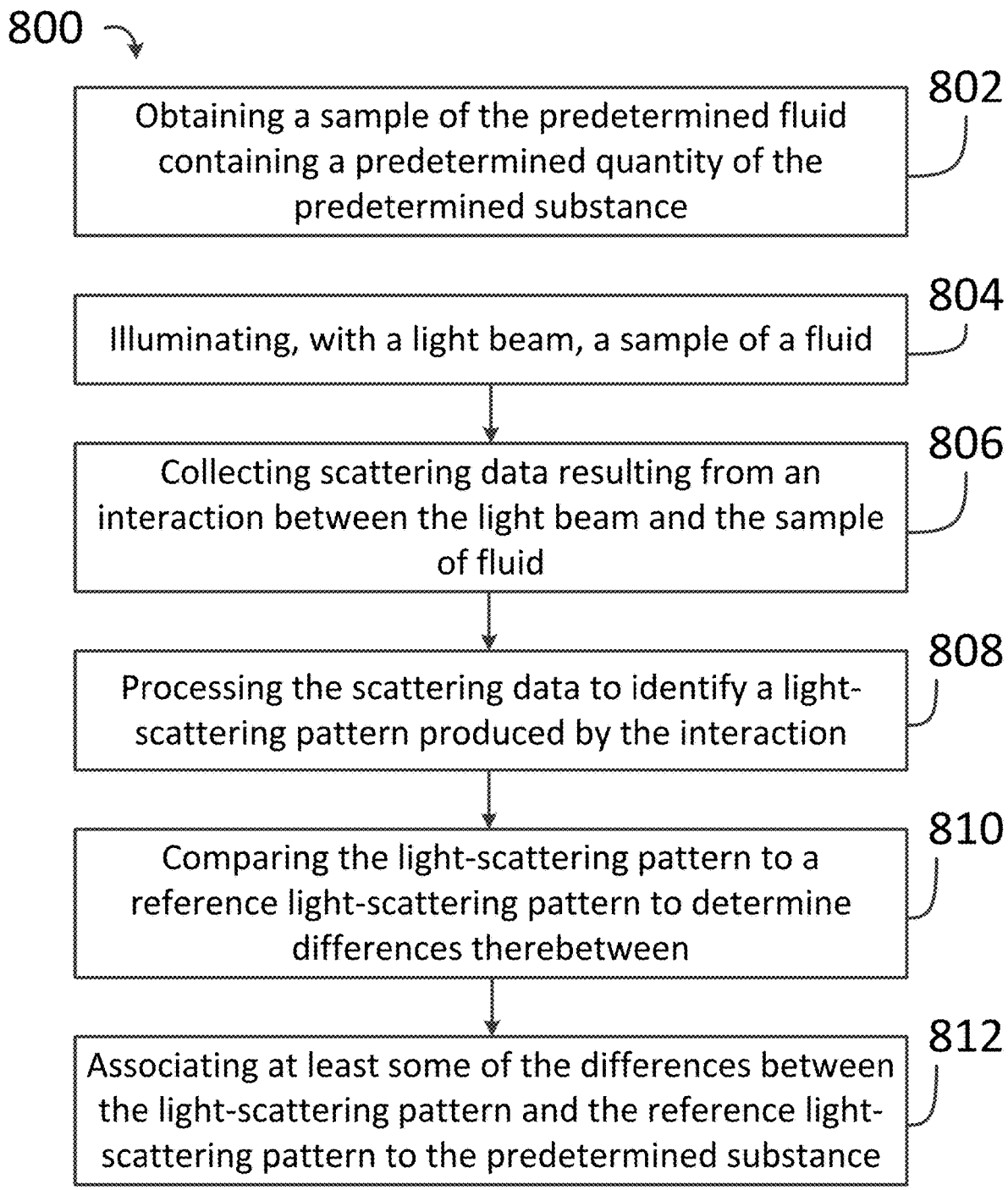
FIG. 8 is a flowchart illustrating an embodiment of a process for determining a light-scattering pattern associated with the presence of a predetermined substance in a predetermined fluid.

With reference to FIG. 6, a method 800 for determining a light-scattering pattern associated with the presence of a predetermined substance in a predetermined fluid is illustrated. The method 800 can be used to identify a "signature" for the predetermined substance, indicative of a scattering pattern produced when the substance is present in the fluid.

At step 802, a sample of the predetermined fluid, containing a predetermined quantity of the predetermined substance, is obtained. For example, a sample of milk containing a predetermined quantity of a particular hormone, such as progesterone, can be obtained. At step 804, the sample of the fluid is illuminated with a light beam. At step 806, light-scattering data resulting from an interaction between the light beam and the sample of fluid is collected. A setup substantially similar to the light-scattering detection system 100 shown in FIG. 1 could be used.

At step 808, the light-scattering data is processed to identify a light-scattering pattern produced by the interaction. At step 810, the light-scattering pattern produced is compared against a reference light-scattering pattern to determine differences between the two. The reference light-scattering pattern can produced by a second interaction between a second light beam and a reference sample of the fluid known not to contain the predetermined substance. For example, a reference sample of milk, known not to contain progesterone, can be used to obtain the reference light-scattering pattern. The differences between the light-scattering pattern of the sample and the reference light-scattering pattern can be used to assess the additional light-scattering produced by the predetermined substance present in the sample.

At step 812, at least some of the differences between the light-scattering pattern of the sample and the reference light-scattering pattern are associated with the predetermined substance. For example, if the light-scattering pattern of the sample exhibits additional scattered light at a particular angle X, at which the reference light-scattering pattern does not, then light scattering at the angle X can be associated with the predetermined substance. In this fashion, when light scattering at the angle X is detected in a subsequent sample, it is understood that the subsequent sample also contains the predetermined substance. In some embodiments, there may be multiple differences, that is to say multiple angles at which light scattering is present in the light-scattering pattern of the sample but not of the reference light-scattering pattern. In some such embodiments, only a single angle is associated with the substance; in some other such embodiments, more than one of the angles is associated with the substance. These angle(s) can be referred to as the "signature" or "response" of the predetermined substance. The processing and analysis hardware and software used in the method 800 can substantially mirror those used in the method 200.

The methods and systems described herein may be implemented in a high level procedural or object-oriented programming or scripting language, or a combination thereof, to communicate with or assist in the operation of a computer system, for example the computing device 510. Alternatively, the methods and systems described herein may be implemented in assembly or machine language. The language may be a compiled or interpreted language. Program code for implementing the methods and systems described herein may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems described herein may also be considered to be implemented by way of a non-transitory computer-readable storage medium having a computer program stored thereon. The computer program may comprise computer-readable instructions which cause a computer, or more specifically the processing unit 512 of the computing device 510, to operate in a specific and pre-defined manner to perform the functions described herein, for example those described in the method 200, 700, and/or 800.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the methods and systems described herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for assessing a health state of a lactating mammal, comprising:
    illuminating, with a light beam, a sample of milk obtained from the lactating mammal, wherein the light beam comprises light of at least a first wavelength;
    collecting scattering data from a set of images received from an imaging device configured to receive forward scattering intensities from an angle greater than 0.5 degrees resulting from an interaction between the light beam and the sample of milk;
    processing the scattering data by comparing, on a pixel-by-pixel basis, each image in set of images to obtain a standard deviation image from the set of images;
    determining a scattering intensity profile defined by a region of interest from a centre point of the scattering data to an outer edge of the scattering data; and
    assessing the health state of the lactating mammal by comparing peaks of the determined scattering intensity profile against at least one reference scattering intensity profile.

2. The method of claim 1, wherein the scattering data is indicative of light from the light beam being scattered along at least a first forward scattering angle greater than 0.5 degrees.

3. The method of claim 1, wherein the light beam comprises light of at least a first wavelength and a second wavelength, and wherein the scattering data is indicative of light from the light beam being scattered along at least a first scattering angle associated with the first wavelength and of light from the light beam being scattered along a second scattering angle associated with the second wavelength, wherein the scattering data comprises a plurality of data sets each associated with a respective scattering angle.

4. The method of claim 1, wherein processing the scattering data comprises comparing the standard deviation of pixel intensity for a set of scattering intensity profiles against the standard deviation of pixel intensity for at least one reference scattering intensity profile, the at least one reference scattering intensity profile associated with known characteristics indicative of the presence of one of antibiotics, progesterone, ketosis, and blood.

5. The method of claim 1, wherein processing the scattering data comprises processing the scattering data using a neural network, and training the neural network using reference milk samples having known characteristics.

6. The method of claim 1, wherein the health state of the lactating mammal is based on the presence of at least one characteristic of the sample of milk comprising at least one of: a fat-to-protein ratio, an antibiotic content, a blood content, or a progesterone content.

7. The method of claim 1, wherein assessing the health state of the lactating mammal comprises determining whether the lactating mammal is likely to be in ketosis.

8. The method of claim 1, wherein assessing the health state of the lactating mammal comprises estimating the progesterone levels of the lactating mammal.

9. The method of claim 1, wherein the sample of milk is illuminated in-line while the lactating animal is being milked.

10. The method of claim 1, wherein the light beam interacts with dissolved substances in the sample of milk.

11. A system for assessing a health state of a lactating mammal, comprising:
    a light source configured to direct a light beam towards a sample of milk obtained from the lactating mammal;
    an imaging device configured to collect scattering data from a set of images received from said imaging device configured to receive forward scattering intensities from an angle greater than 0.5 degrees resulting from an interaction between the light beam and the sample of milk; and
    a processing system communicatively coupled to said imaging device, said processing system comprising:
        a processor; and
        a memory storing instructions which when processed by the processor configure the processor to:
            process the scattering data by comparing, on a pixel-by-pixel basis, each image in set of images to obtain a standard deviation image from the set of images;
            determine a scattering intensity profile defined by a region of interest from a centre point of the scattering data to an outer edge of the scattering data; and
            assessing the health state of the lactating mammal by comparing peaks of the determined scattering intensity profile against at least one reference scattering intensity profile.

12. The system of claim 11, wherein the scattering data is indicative of light from the light beam being scattered along at least a first forward scattering angle greater than 0.5 degrees.

13. The system of claim 11, wherein the light beam comprises light of at least a first wavelength and a second wavelength, and wherein the scattering data is indicative of light from the light beam being scattered along at least a first scattering angle associated with the first wavelength and of light from the light beam being scattered along a second scattering angle associated with the second wavelength, wherein the scattering data comprises a plurality of data sets each associated with a respective scattering angle.

14. The system of claim 11, wherein processing the scattering data comprises comparing the standard deviation of pixel intensity for a set of scattering intensity profiles against the standard deviation of pixel intensity for at least one scattering intensity profile, the at least one scattering intensity profile associated with known characteristics indicative of the presence of one of antibiotics, progesterone, ketosis, and blood.

15. The system any claim 11, wherein the processing system implements a neural network, and wherein to process the scattering data the processor is configured to process the scattering data using the neural network, and train the neural network using reference milk samples having known characteristics.

16. The system of claim 11, wherein the health state of the lactating mammal is based on the presence of at least one characteristic of the sample of milk comprising at least one of: a fat content, a fat-to-protein ratio, an antibiotic content, a blood content, or a progesterone content.

17. The system of claim 11, wherein to assess the health state of the lactating mammal the processor is configured to determine whether the lactating mammal is likely to be in ketosis.

18. The system of claim 11, wherein to assess the health state of the lactating mammal the processor is configured to estimate the progesterone levels of the lactating mammal.

19. The system of claim 11, wherein the sample of milk is illuminated in-line while the lactating animal is being milked.

20. The system of claim 11, wherein the light beam interacts with dissolved substances in the sample of milk.

* * * * *